United States Patent [19]

Raccach

[11] 4,342,786

[45] * Aug. 3, 1982

[54] METHOD FOR FERMENTING VEGETABLES

[75] Inventor: Moshe Raccach, Tempe, Ariz.

[73] Assignee: Microlife Technics, Inc., Sarasota, Fla.

[*] Notice: The portion of the term of this patent subsequent to Dec. 1, 1998, has been disclaimed.

[21] Appl. No.: 268,356

[22] Filed: May 29, 1981

Related U.S. Application Data

[63] Continuation-in-part of Ser. No. 114,760, Jan. 24, 1980, Pat. No. 4,303,679.

[51] Int. Cl.³ .................... A23B 7/10; A23L 1/218
[52] U.S. Cl. .................................................. 426/52
[58] Field of Search ........................... 426/52, 56, 59; 435/139, 253, 822

[56] References Cited

U.S. PATENT DOCUMENTS 2,945,766 7/1960 Chaiet .................................. 99/107
3,932,674 1/1976 Etchells et al. ...................... 426/52
4,238,513 12/1980 Satz ..................................... 426/59

Primary Examiner—Lionel M. Shapiro
Attorney, Agent, or Firm—Ian C. McLeod

[57] ABSTRACT

A method is described for producing fermented vegetables by generating lactic acid in an acidic brine solution using selected cultures of Pediococcus pentosaceus which have rapid low temperature fermentation characteristics. The preferred Pediococcus pentosaceus is NRRL-B-11,465 which effectively and rapidly removed brine carbohydrate thus lowering the pH at unusually low brine temperatures less than about 25° C. (77° F.) and at high salinity. A stimulatory food grade, metal salt, preferably a manganese salt, is provided in the acidic brine solution with the Pediococcus pentosaceus to accelerate growth and reduce the fermentation time. The method is particularly adapted to the controlled fermentation of cucumbers in making pickles.

16 Claims, No Drawings

METHOD FOR FERMENTING VEGETABLES

CROSS REFERENCE TO RELATED APPLICATION

This application is a continuation-in-part of application Ser. No. 114,760, filed Jan. 24, 1980, now U.S. Pat. No. 4,303,679, issued Dec. 1, 1981.

BACKGROUND OF THE INVENTION

The present invention relates to a method for fermenting vegetables in an acidic brine solution using selected cultures of *Pediococcus pentosaceus* having rapid low temperature fermentation characteristics. The present invention particularly relates to the use of *Pediococcus pentosaceus* in the presence of a stimulatory food grade metal ion, preferably a manganese ion, in the brine.

PRIOR ART

The prior art in the controlled bulk vegetable fermentation field is represented by U.S. Pat. No. 3,932,674 to Etchells et al where lactic acid producing bacteria are used to remove naturally occurring carbohydrates thereby generating the lactic acid. This patent describes the use of *Lactobacillus plantarum* or *Pediococcus cerevisiae* for the fermentations at 65° F. (18.3° C.) to 90° F. (32.2° C.) although 78° F. to 85° F. (25.6° to 29.4° C.) is preferred. The vegetables are preliminarily treated in the brine solution (preferably about 6.6% sodium chloride) and sanitized to eliminate the natural bacterial or yeast flora by the addition of chlorine (about 80 ppm) and by means of the use of non-toxic acids. The acid is generally acetic acid, particularly vinegar and the pH is reduced to about 3.1 to 3.3. The brine solution is then neutralized to a pH of about 4.2 to 4.8 and lactic acid producing bacteria are added to the brine, preferably in a concentration between about 1 to about 10 billion per gallon of the vegetable-brine mixture. In the Etchells process, carbon dioxide, which causes defects in the pickles, is purged from the brine solution using a non-reactive gas such as nitrogen which is bubbled through the solution.

In the southern parts of the United States where the ambient air temperatures are relatively warm, it is not difficult to maintain an optimal bulk fermentation temperature of about 80° to 85° F. (26.7° C. to 29.4° C.). At these temperatures the fermentation is completed in about 10 to 14 days. As the ambient air temperatures are reduced in the northern regions of the United States, the fermentation period is considerably lengthened. There has been a need for bacterial cultures which will function rapidly at temperatures which are significantly lower, e.g. on an average in the 60° F. to 65° F. (15.6° to 18.3° C.) range and generally less than 77° F. (25° C.). The problem is that the highly saline solution having a relatively low pH retards the growth of most lactic acid producing bacteria at the lower temperatures.

In my prior application, I described the use of stimulatory, food grade metal salts, particularly manganese salts in the fermentation of meats using the unique strains of *Pediococcus pentosaceus* of the present invention. Satz U.S. Pat. No. 4,238,513 describes the use of *Pediococcus pentosaceus* ATCC 10,791 or NRRL-B-11,465 in meat fermentations. U.S. Pat. No. 2,945,766 to Chaiet describes the use of such manganese salts with conventionally used lactic acid producing bacteria for meat fermentations.

It has now been found that certain food grade metal salts are significantly stimulatory to the unique *Pediococcus pentosaceus* in acidic brine solutions. This is true even though the starting pH for the fermentation in the acidic brine is quite low (pH 4.8 or lower) as compared to a meat fermentation where pH 4.8 would be the final pH.

OBJECTS

It is therefore an object of the present invention to provide a method for producing fermented vegetables in an acidic brine using selected cultures of *Pediococcus pentosaceus*. It is particularly an object of the present invention to provide a method wherein the *Pediococcus pentosaceus* are able to effectively and rapidly remove brine carbohydrate in the presence of a relatively low acidity, about pH 4.8 or lower produced by adding acetic acid which is bactericidal, in the brine and at relatively low temperatures. These and other objects will become increasingly apparent from the reference to the following description.

GENERAL DESCRIPTION

The present invention relates to the improvement in the method for fermenting vegetables by the addition of a lactic acid producing bacterium to an acidic brine solution having an initial pH of less than about 4.8 to ferment carbohydrates in the solution which comprises providing an effective concentration of a food grade metal salt stimulated *Pediococcus pentosaceus* which can effectively and rapidly remove carbohydrate from the brine at temperatures less than about 25° C. (77° F.) wherein the *Pediococcus pentosaceus* are provided in the brine as a concentrate containing at least about $1 \times 10^7$ cells per ml. The improvement of the present invention particularly includes the use of a stimulatory food grade metal ion in the acidic brine solution in an amount sufficient to accelerate the growth of the *Pediococcus pentosaceus* at temperatures of less than about 25° C. (77° F.). Manganese salts are particularly preferred and in this group of salts manganese sulfate hydrate is the most preferred.

The present invention particularly relates to the improved method for fermenting vegetables by the addition of a lactic acid producing bacterium to an acidic brine solution having an initial pH of less than about 4.8 to ferment carbohydrate in the solution, which comprises providing an effective concentration of a *Pediococcus pentosaceus* in the brine which can effectively and rapidly remove the carbohydrate from the brine at a temperature of less than 25° C. (77° F.) along with an amount of a stimulatory, food grade metal salt sufficient to stimulate the growth of the *Pediococcus pentosaceus* at less than about 25° C. (77° F.).

The selected *Pediococcus pentosaceus* is described in my co-pending application Ser. No. 114,760. Thus the preferred *Pediococcus pentosaceus* strain of the present invention has been deposited at the Northern Regional Research Laboratory of the USDA, Peoria, Ill. and has been designated as NRRL-B-11,465 and is freely available upon ordering by the reference number. NRRL-B-11,465 or a strain of the same species which has substantially the same low meat temperature fermentation characteristics is used in the present invention, such as strains produced by genetic manipulation, including mutation.

*Pediococcus pentosaceus* NRRL-B-11,465 was derived from a culture originally deposited at the American Type Culture Collection as ATCC 10,791 and was found as a contaminant in a cucumber brine. This original culture was inaccurately described as being most active at 26° C. (78.8° F.) in a standard culture broth. Actually the culture is most active at 43.3° C. (110° F.). It has different fermentation characteristics from ATCC 25,744 which is the usual strain for this species. The inventor is uncertain as to whether NRRL-B-11,465: (1) is a mutant; or (2) is a selected single strain variant having anomalous low temperature fermentation characteristics.

The selected *Pediococcus pentosaceus* cells are used as a concentrate containing at least about $1 \times 10^7$ to $10^{14}$ cells per ml, usually between about $1 \times 10^9$ and $1 \times 10^{12}$ cells per ml, preferably mixed with the metal salt, particularly manganese salts. The concentrate should have a pH between about 4 to 8 to prevent damage to the cells upon storage. The concentrate alone or containing the metal salt can be frozen with or without a freezing stabilizing agent such as monosodium glutamate, malt extract, low fat dry milk, alkali metal glycerophosphates, glutamic acid, cystine, glycerol, dextran or the like and then thawed for use or it can be lyophilized to a powder as is well known to those skilled in the art.

The cells are preferably used at a concentration between about 0.1 billion to 10 billion cells per gallon (3.79 liters) of brine. The metal salt is used in an amount of the metal cation in the salt above about $1 \times 10^{-10}$ grams to about $1 \times 10^{-3}$ grams per milliliter of the brine, preferably between about $10^{-9}$ and $10^{-5}$ gram per ml of brine. The brine is exclusive of the vegetables in each instance. The salt must be stimulatory and food grade. Such salts include for instance, manganese chloride, manganese sulfate, manganese citrate, manganese glycerophosphate, manganese oxide and manganese gluconate and the various non-toxic metal salts of acids which are at least slightly soluble in water or the acidic brine. Other metal cations include ferrous, ferric, magnesium, calcium, zinc; however, none is as nearly effective as manganese. The metal salt can be incorporated into the culture in an amount between about 0.01 percent and 50 percent by weight of the culture in order to provide the amount of the metal salt needed in the brine and vegetable mixture when the culture is added.

SPECIFIC DESCRIPTION

Example 1

In this example the *Pediococcus pentosaceus* NRRL-B-11,465 concentrate contained about 6.288% by weight of manganese sulfate as the hydrate (formula weight 169.02), which is equivalent to 2.044% manganese ion. The concentrate contained about $300 \times 10^9$ cells per ml of viable cells. In the manner of Etchells et al U.S. Pat. No. 3,932,694 green cucumbers were equilibrated by placing them in a 6.6 percent sodium chloride solution and submerging them for 24 hours at 24° C. The salinity was maintained at a level of about 6.6% sodium chloride. The pH of the brine was then adjusted to 3.3 with acetic acid and then readjusted to pH 4.7 with sodium hydroxide. The acidification step helps to reduce the natural flora that may be present in the brine because of the cucumbers.

The brine containing the cucumbers was inoculated with the *Pediococcus pentosaceus* and was maintained at 24° C. (75.2° F.) as shown in Table I.

TABLE I

| Test | (g) Cucumber | (ml) Brine-6.6% NaCl | Viable Culture Inoculation Rate |
|---|---|---|---|
| Control | 600 | 325 | None |
| *Pediococcus pentosaceus* | 630 | 340 | 2.91 ml of a $10^{-3}$ dilution with water |
| *Pediococcus pentosaceus* | 620 | 335 | 2.8 ml of a $10^{-3}$ dilution with water |

The *Pediococcus pentosaceus* had a viable cell count of $2.57 \times 10^6$ cells per milliliter of brine and $1.75 \times 10^{-8}$ grams manganese ion per ml of brine.

The pH of the brine solutions was determined daily. The reducing sugar content of the solutions was determined daily using a detection strip which quantitatively detects the presence of reducing sugars (Keto-diastrix ® manufactured by Ames Division, Miles Laboratories, Elkhart, Indiana). The results are shown in Table II.

TABLE II

| Test | Day 0 pH | Day 0 Sugar | Day 4 pH | Day 4 Sugar | Day 8 pH | Day 8 Sugar | Day 10 pH | Day 10 Sugar |
|---|---|---|---|---|---|---|---|---|
| Control | 4.5 | +++ | 4.4 | +++ | 4.3 | +++ | 4.1 | ++ |
| *Pediococcus pentosaceus* | 4.5 | +++ | 3.9 | ++ | 3.4 | + | 3.3 | 0 |
| *Pediococcus pentosaceus* | 4.5 | +++ | 3.85 | ++ | 3.5 | + | 3.3 | 0 |

Based upon the results shown in Table II, *Pediococcus pentosaceus* NRRL-B-11,465 lowered the pH of the brine and removed carbohydrate from the cucumbers at 24° C. (77° F.) in 10 days. The method is thus very rapid at normal temperatures of 24° C. (75.2° F.) in the presence of the manganese salt. Under similar conditions with *Lactobacillus plantarum* and other Pediococcus species the results are comparable to the uninoculated control at 24° C. (75.2° F.).

Example 2

The method of Example 1 was repeated at 18° C. (64.4° F.).

The results are shown in Table III.

TABLE III

| | Control | | *Pediococcus pentosaceus* NRRL-B-11,465 | |
|---|---|---|---|---|
| Day | pH | Sugar | pH | Sugar |
| 0 | 4.5 | +++ | 4.5 | +++ |
| 1 | 4.5 | +++ | 4.5 | +++ |
| 2 | 4.4 | +++ | 4.4 | +++ |
| 3 | 4.3 | +++ | 4.3 | ++ |
| 4 | 4.4 | +++ | 4.3 | + |
| 7 | 4.3 | +++ | 4.2 | + |
| 11 | 4.3 | +++ | 4.1 | + |
| 14 | 4.1 | +++ | 3.9 | + |
| 18 | 4.1 | +++ | 3.6 | + |
| 21 | 4.1 | +++ | 3.5 | + |
| 25 | 4.1 | +++ | 3.5 | 0 |

The *Pediococcus pentosaceus* NRRL-B-11,465 rapidly removed the carbohydrate from the brine at the low temperature of 18° C. (64.4° F.) and the fermentation was completed in 25 days. Under similar conditions *Lactobacillus plantarum* of other Pediococcus species are comparable to the uninoculated control at 18° C. (64.4° F.).

Example 3

The process of Example 1 was repeated on a large scale using tanks having a capacity of 1700 bushels and 1200 bushels of cucumbers in brine in a plant which had a very high percentage of "bloaters", which are not commercially acceptable. The results are shown in Table IV.

TABLE IV

|  | % Acceptable | Lactic Acid % | Days Fermented |
|---|---|---|---|
| *Pediococcus pentosaceus* NRRL-B-11,465 20° C. (68° F.) 1200 bushels) | 97 | 1.05 | 8 |

When no culture was used in the brine cucumber mixture and the natural flora was relied upon for the fermentation, the same plant had an average of the high 70's to 86% acceptable yield. Thus *Pediococcus pentosaceus* NRRL-B-11,465 at 20° C. (68° F.) effectively reduces carbohydrate from the brine and effectively eliminates the incidence of bloating.

As can be seen from the foregoing description, *Pediococcus pentosaceus* NRRL-B-11,465 provides a significantly improved method for fermenting vegetables in acidic brines in order to remove the carbohydrates and convert them to lactic acid at low temperatures. Commercially the invention is regarded as important in the processing of very large volumes of cucumbers in brine solutions with a reduced incidence of bloating that usually occurs.

*Pediococcus pentosaceus* NRRL-B-11,465 does not function as well without the added metal ion for stimulation at low temperatures. The reasons for this result are not understood.

I claim:

1. In the method for fermenting vegetables by the addition of a lactic acid producing bacterium to an acidic brine solution having an initial pH of less than about 4.8 to ferment carbohydrate in the solution the improvement which comprises:
providing an effective concentration of a food grade metal salt stimulated *Pediococcus pentosaceus* in the brine which can effectively and rapidly remove carbohydrate in the brine at a temperature of less than about 25° C. wherein the *Pediococcus pentosaceus* are provided in the brine as a concentrate containing at least about $1 \times 10^7$ cells per ml of concentrate.

2. The method of claim 1 wherein the brine has a salinity of about 6.6% sodium chloride.

3. The method of claim 1 wherein the brine solution is purged with a non-reactive gas to remove carbon dioxide.

4. The method of claim 1 wherein the vegetables are cucumbers.

5. The method of claim 1 wherein the fermentation is at less than about 18° C. for a period of up to 25 days.

6. The method of claim 1 wherein the brine solution contains an amount of a stimulatory food grade metal salt sufficient to accelerate the growth of the *Pediococcus pentosaceus*.

7. The method of claim 6 wherein the metal salt is manganese sulfate hydrate.

8. The method of claim 6 wherein the brine solution contains between about $10^{-10}$ and $10^{-3}$ grams per milliliter of a manganese salt as the metal ion.

9. The method of claim 1 wherein the *Pediococcus pentosaceus* has the fermentation characteristics of NRRL-B-11,465.

10. The method of claim 9 wherein the *Pediococcus pentosaceus* is NRRL-B-11,465.

11. The method of claim 1 wherein the *Pediococcus pentosaceus* rapidly ferments the sugars in the brine at temperatures of about 18° C.

12. In the method for fermenting vegetables by the addition of a lactic acid producing bacterium to a brine solution having an initial pH of less than about 4.8 to ferment carbohydrates in the solution the improvement which comprises providing an effective concentration of a *Pediococcus pentosaceus* in the brine which can effectively and rapidly remove the carbohydrate in the brine at a temperature of less than 25° C. along with an amount of a stimulatory, food grade metal salt sufficient to stimulate the growth of the *Pediococcus pentosaceus* at less than about 25° C.

13. The method of claim 12 wherein the metal salt is a manganese salt.

14. The method of claim 13 wherein the manganese salt is manganese sulfate.

15. The method of claim 12 wherein the *Pediococcus pentosaceus* has the fermentation characteristics of NRRL-B-11,465.

16. The method of claim 15 wherein the *Pediococcus pentosaceus* is NRRL-B-11,465.

* * * * *